(12) United States Patent
Morales et al.

(10) Patent No.: US 10,368,903 B2
(45) Date of Patent: Aug. 6, 2019

(54) WIDTH-ADJUSTABLE CUTTING INSTRUMENT FOR TRANSAPICAL AORTIC VALVE RESECTIONING

(71) Applicant: Aesculap AG, Tuttlingen (DE)

(72) Inventors: Pedro Morales, Tuttlingen (DE); Dieter Weisshaupt, Immendingen (DE)

(73) Assignee: Aesculap AG (DE)

( * ) Notice: Subject to any disclaimer, the term of this patent is extended or adjusted under 35 U.S.C. 154(b) by 945 days.

(21) Appl. No.: 14/432,631

(22) PCT Filed: Sep. 30, 2013

(86) PCT No.: PCT/EP2013/070363
§ 371 (c)(1),
(2) Date: Mar. 31, 2015

(87) PCT Pub. No.: WO2014/053446
PCT Pub. Date: Apr. 10, 2014

(65) Prior Publication Data
US 2015/0238218 A1    Aug. 27, 2015

(30) Foreign Application Priority Data

Oct. 4, 2012 (DE) .................. 10 2012 109 459

(51) Int. Cl.
*A61B 17/3209* (2006.01)
*A61B 17/32* (2006.01)
(Continued)

(52) U.S. Cl.
CPC .. *A61B 17/3209* (2013.01); *A61B 17/320016* (2013.01); *A61B 17/32053* (2013.01);
(Continued)

(58) Field of Classification Search
CPC ........ A61B 17/3209; A61B 17/320016; A61B 17/32053; A61B 2017/22097;
(Continued)

(56) References Cited

U.S. PATENT DOCUMENTS 3,667,474 A    6/1972  Lapkin
6,830,584 B1   12/2004 Seguin
(Continued)

FOREIGN PATENT DOCUMENTS

CN    2130506    4/1993
DE    60017189   9/2005
(Continued)

OTHER PUBLICATIONS

Chinese Office Action dated Aug. 22, 2016 for Chinese Application No. 201380060959.8, including English translation, 17 pages.
(Continued)

*Primary Examiner* — Todd J Scherbel
*Assistant Examiner* — Chima U Igboko
(74) *Attorney, Agent, or Firm* — RatnerPrestia

(57) ABSTRACT

A surgical cutting instrument for transapical aortic valve resection includes a cutting unit arranged on the distal end of a tool shaft and at least one mechanical cutting element for making a circular incision. The at least one cutting element can be adapted, in particular continuously adapted to different aortic diameters by means of a radially movable actuating mechanism.

28 Claims, 12 Drawing Sheets

(51) Int. Cl.
*A61B 17/3205* (2006.01)
*A61B 17/22* (2006.01)
*A61B 17/3207* (2006.01)

(52) U.S. Cl.
CPC .............. *A61B 2017/22097* (2013.01); *A61B 2017/320716* (2013.01)

(58) Field of Classification Search
CPC ........... A61B 2017/22098; A61B 2018/00369; A61B 17/3205; A61B 17/3207; A61B 17/320758; A61B 17/32056; A61B 2017/320733; A61B 2017/320741; A61B 17/32075; A61B 17/320725; A61F 2/2427; A61F 2/2442
USPC ................ 604/104, 105, 106, 107, 108, 109
See application file for complete search history.

(56) References Cited

U.S. PATENT DOCUMENTS

| | | |
|---|---|---|
| 2005/0075659 A1 | 4/2005 | Realyvasquez |
| 2005/0209617 A1 | 9/2005 | Koven |
| 2006/0271081 A1* | 11/2006 | Realyvasquez ...... A61B 17/115 606/170 |
| 2007/0185513 A1* | 8/2007 | Woolfson ......... A61B 17/32002 606/108 |
| 2008/0188880 A1 | 8/2008 | Fischer |
| 2008/0255595 A1* | 10/2008 | Buchbinder ... A61B 17/320725 606/159 |
| 2013/0116500 A1 | 5/2013 | Kohl |
| 2014/0213933 A1* | 7/2014 | Real ................... A61B 10/0266 600/567 |

FOREIGN PATENT DOCUMENTS

| | | |
|---|---|---|
| DE | 102007005900 | 8/2008 |
| DE | 102010009723 | 9/2011 |
| WO | 2012100185 | 7/2012 |
| WO | 2013135792 | 9/2013 |

OTHER PUBLICATIONS

German Search Report for German Application No. 10 2012 109 459.4 dated Jun. 11, 2013.
International Search Report for International Application No. PCT/EP2013/070363 dated Jan. 2, 2014.

* cited by examiner

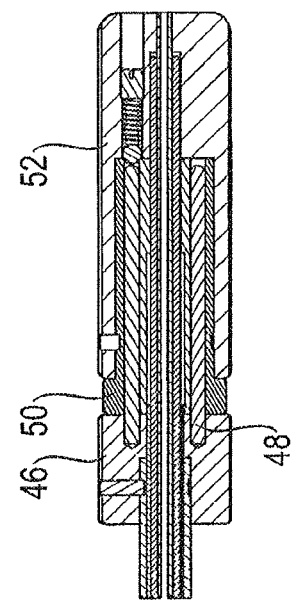
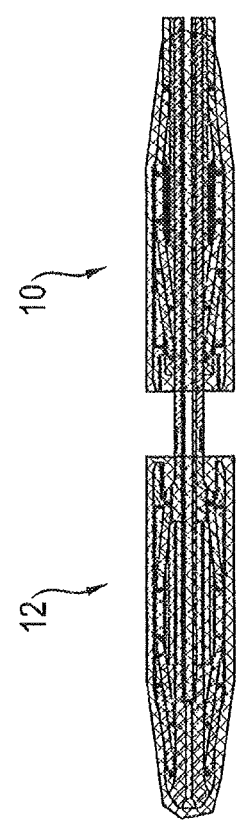
Fig. 4

WIDTH-ADJUSTABLE CUTTING INSTRUMENT FOR TRANSAPICAL AORTIC VALVE RESECTIONING

RELATED APPLICATIONS

This application is the U.S. National Phase of International Application No. PCT/EP2013/070363, filed Sep. 30, 2013, which claims the benefit of priority of German Application No. DE 10 2012 109 459.4, filed Oct. 4, 2012, the contents of both applications being incorporated by reference herein in their entireties.

FIELD

The present invention relates to a surgical, in particular endoscopic cutting instrument for transapical aortic valve resection.

BACKGROUND

In the event of an aortic valve stenosis or insufficiency, a surgical procedure is indicated in many cases, in which the body's own aortic valve is replaced by an artificial aortic valve. Apart from the open surgical operation which is carried out under general anesthetic and by use of a heart-lung apparatus and in which the sternum is opened up using a saw, the heart is exposed and has to be stopped, the aortic valve can also be replaced in a minimally invasive procedure on the beating heart. In doing so, an access route via the femoral artery (transfemoral) or via the cardiac apex (transapical) is selected.

One possible way is the introduction of an aortic valve prosthesis which expands by itself or is expanded by means of a balloon and displaces the body's own aortic valve. However, the bloodstream may be impaired by undefined lateral openings which are generated between the artificial aortic valve and the aortic wall if the natural aortic valve is not removed but crushed against the aortic wall by the artificial aortic valve.

In this regard, it is recommended to first remove the body's own aortic valve prior to inserting the artificial aortic valve.

Regarding the aortic valve resection, many solutions are known in which the calcified aortic valve is cut out with a laser. There are also publications, however, according to which the calcified aortic valve (in the laboratory and on a pig) has been removed by an "aorta punching device".

The process of separating the calcified aortic valve with laser technology is very time-consuming and not very precise, too. The removal of a valve with an "aorta punching device" is not feasible at present, as the rigid punching head already matched with the inner diameter of the aorta has to be passed through the constricted aortic valve and chalky particles deposited on the aortic valve may come loose and find their way into the blood circulation, which might result in a thrombosis. Here, a further problem is the fact that the aortic diameters vary in the range between approximately 15 mm and 35 mm, so that a rigid punch head does not have the optimum diameter in the majority of cases, which in turn has the consequence that the provided aortic valve inserted therein does not have the optimum fit.

SUMMARY

Thus, it is the object of the present invention to provide a surgical cutting tool for an aortic valve resection, which allows the best possible fit of the new artificial aortic valve, without the phenomenon of chalky plaque coming loose from the valve and finding their way into the bloodstream.

A surgical, in particular endoscopic, cutting instrument according to the invention is suitable in particular for a transapical aortic valve resection. It comprises a cutting unit arranged on the distal end of a tool shaft and comprising at least one mechanical cutting element for making a circular incision. Said cutting element may comprise, for example, an annular blade or may be implemented as a blade which is rotatable around the longitudinal axis of the shaft. According to the invention, the at least one cutting element can be adjusted in its width via an actuating or spreading mechanism, in particular in continuously variable fashion. Specifically, the radial distance between the at least one cutting element and the longitudinal axis of the shaft (i.e. the cutting diameter) can be adapted to different aortic diameters.

The present invention provides a surgical cutting instrument whose diameter can be precisely adapted to the anatomic circumstances of the aorta, in particular to the aortic diameter, so that one and the same instrument can be used for the resection of aortic valves in different sizes and diameters and precisely adapted in each case, instead of being forced to produce and use different instruments for different aortic diameters.

The precise adaptation to the respective circumstances further allows the achievement of an optimum fit of the new artificial aortic valve and ensures, among other things, that the aortic valve reliably claws into the aorta and hence cannot migrate any more. The actual function of the valve (flow control) is also enhanced, because it is able to deploy on-site preferably to the full extent and in circular shape. This optimizes the blood flow, because it is not impaired any longer by undefined lateral openings—as explained at the outset—if the natural aortic valve is removed.

According to one aspect of the invention, not only the at least one cutting element, but the cutting unit as a whole can be adjusted in its width, in particular in continuous fashion. If the cutting unit is composed of an actuating mechanism and cutting elements arranged thereon and the outer dimensions of the cutting unit are defined merely by the radially movable actuating mechanism, a radial movement of the actuating mechanism does not only allow for the alteration of the cutting diameter, but also for the folding or expanding of the cutting unit as a whole. This width adjustment of the entire cutting unit allows to reduce the outer dimensions of the cutting unit on the whole to such an extent that it is also capable of diving through a very narrow aortic valve affected by a stenosis, without chalky particles coming loose in this process, before the cutting unit or a part of the cutting unit is again expanded to the aortic diameter behind the aortic valve.

Further, the proximal tool shaft is provided with a tool handle for holding and maneuvering the tool shaft, and with a handle piece (rotary knob) for a manual width adjustment of the cutting element. In this way, the cutting element can be manually adjusted in its active (effective) cutting diameter even if it is already in the functional cutting position.

According to one aspect of the invention, the cutting unit is formed by a cutting tool which is rotatably supported around the tool shaft and comprises at least one cutting blade whose radial distance to the rotational axis or tool shaft axis can be (in particular continuously) adjusted and in this way can be matched with different aortic diameters.

The radial distance of the cutting blade can be altered in a simple manner if the cutting blade is arranged on a supporting arm in fixed or detachable fashion, said supporting arm being radially movable via the actuating mechanism, for instance in outward direction. Thus, the cutting unit can be inserted into the heart and through the natural aortic valve in the folded or compacted state and then can be expanded or spread to the respective aortic diameter. If need be, the cutting unit can be made smaller or folded again after the cutting process.

According to an aspect of the invention, the cutting blade may be arranged such that it extends in the axial direction or in a direction parallel to the tool shaft axis and performs the cut in the rotational or circumferential direction.

In order to prevent the blade(s) from injuring any tissue during the insertion of the instrument, the blade(s) may be arranged contrary to the insertion direction or may point toward the proximal side of the tool shaft.

The actuating mechanism may be designed such that one or more supporting arms distributed in the circumferential direction and supporting cutting blades can be expanded and retracted parallel to the tool shaft axis, so that the cutting blade(s) always remain(s) axially parallel or in parallel alignment relative to the tool shaft axis throughout the entire adjustment range. A so-called parallelogram-type mechanic system may be used for the parallel translation of the supporting arm.

The higher the number of cutting blades distributed on the cutting tool, the smaller is the rotary motion of the cutting tools which is required for the cutting process in order to carry out a cut by 360°.

The supporting arms allow for the centering of the cutting tool within the aortic inner wall. This is why the cutting tool preferably comprises at least 3 supporting arms.

The use of three cutting blades which are arranged on three supporting arms distributed with a distance of respectively 120°, constitutes a good compromise between a space-saving stowage of the supporting arms and the associated actuating mechanism, on the one hand, and the smallest possible rotary motion on the other hand.

According to one aspect of the invention, the entire distal portion of the tool shaft or at least the cutting tool together with the cutting blades can be detached from the tool shaft. This allows for the detachment of the cutting tool from the instrument after the cutting process and for its recovery in some other way. This modular construction further allows a simple replacement of the cutting tool without the need to replace the entire instrument as a whole.

According to another aspect of the invention, the cutting unit is not formed by a cutting tool comprising a rotatable cutting blade, but by a punch-die assembly movable relative to each other at least in the axial direction. Here, the punch unit and/or the die unit comprises a thin, elastically bendable foil which is bent into a ring and overlaps in the circumferential direction and whose edge forms an essentially annular blade. The diameter of said annular blade can thus be continuously adapted to different aortic diameters by rolling up or unwinding the foil or by a relative displacement of the foil ends in the circumferential direction.

The basic principle of said cutting unit acting as a punch is based on the use of a thin and elastic foil which indeed is very flexible in the longitudinal direction and can be bent or rolled up into an arc, a ring or even to a further extent, but which has a relative sharp and stiff edge in the transverse direction. The process of annularly bending the foil, the foil band or strip and by a corresponding arrangement of the foil around the longitudinal axis of the shaft, said foil produces in the axial direction, i.e. in the punching or cutting direction, a relative stiff punching or cutting unit and achieves a sort of "Coke can effect".

In this arrangement, the foil is arranged on the side facing the die unit or punch unit. By a corresponding actuation of the punch-die assembly, the aortic valve or any other tissue to be severed can be clamped and stamped out or cut between the punch and the die; here, at least one of these two elements comprises the annular blade or foil.

A further advantage of such a foil blade which can be adjusted in width is—in addition to the cost-effective production—the easy fixing ability of the foil in the cutting unit as well as the automatic width adjustment of the foil. Due to the elasticity of the foil, the latter strives to return to its initial state again after an elastic bending deformation. In other words, the foil tends to automatically unroll after having been rolled up. This radial pretensioning force can be utilized, on the one hand, for a fixation in a corresponding mount in the cutting unit (force-fit) and, on the other hand, a suitable radial foil guide allows to control this roll-up process such that the foil or the punching unit can be enlarged in its diameter relatively precisely and in circular fashion, without the need of actively enlarging the diameter of the foil bent into the ring. The foil automatically follows a width adjustment of the foil guide or foil mount toward a larger diameter.

According to one aspect of the invention, the length of the foil can be selected such that it is longer than the circumference of the largest adjustable cutting diameter. This ensures that the foil ends of the foil always overlap, allowing not only to achieve a closed annular blade, but also providing the possibility that the exterior foil end radially supports and guides the interior foil end, for instance in a subsequent decrease of the diameter and during coiling up the foil. In this way, it is ensured throughout the entire adjustment range that the foil ends guide themselves.

According to one aspect of the invention, the punch unit and/or the die unit may comprise an annular assembly of several bent, thin and elastically bendable foils which overlap in the circumferential direction and whose edges form an essentially annular blade whose diameter can be continuously adapted to different aortic diameters by a relative movement of the foils in the circumferential direction. In this case, not a single foil bent into a ring is used, but several foils arranged one behind the other and bent into a ring are used, with neighboring foils overlapping each other. It may be provided in particular that there is a multitude of identical foils or foil segments which are uniformly distributed in the circumferential direction.

The use of a multitude of foils strung together and partially overlapping in the circumferential direction instead of a single foil which is bent into a circle and overlaps in the circumferential direction increases the width adjustment range. Actually, it has turned out that—with a single foil and a large adjustment range of the blade diameter—the foil has to be coiled several times for reaching the small blade diameters. Due to coiling up the foil several times, not only the frictional force of the foils among each other increases with each winding (cf. belt friction), but it may also happen that the foils gape open at some places, which is detrimental to the cutting effect. However, a number of shorter foil segments does not show this phenomenon and exhibits a lower frictional or clamping force during reducing the cutting diameter and rolling up the foil segments than a single foil which is coiled several times.

In similar fashion as described above, the overall length of all foils should be longer than the circumference of the largest adjustable cutting diameter. In order to improve the mutual radial guidance of the foils or to facilitate it at all, the foils overlap in the circumferential direction one by one alternating on the outside and inside. This is why the foils slide on each other so as to get coiled or unrolled.

Preferably, the employed foil is a thin, flexible metal foil. For increasing elasticity, the metal foil may also consist of a superelastic material such as Nitinol, for example.

In order to further increase the cutting or punching performance of the foil, the foil or its side edge(s) may be provided with a bevel.

In addition or as an alternative, the foil may have a cutting geometry with which the entire blade does not come into contact at one go with the tissue to be severed, reducing the punching and cutting forces. This may be achieved in particular by a serrated, wavy or slanted cutting edge.

For adjusting the width of the foil blade, the punch unit and/or the die unit comprises foil guides which can be adjusted in width via the actuating mechanism. The foil(s) is/are axially and radially fixed in the foil guides in such a manner that they can move in the circumferential direction during the width adjustment of the actuating mechanism or upon a radial movement of the foil guides.

For coiling and unrolling the foil or the foil segments, they must have the opportunity to get coiled in the circumferential direction and to be bent inwards to an even larger extent or to get unrolled and further unbent. The axial supporting absorbs the punching and cutting forces. The radial guide controls the diameter adjustment of the foil blade. In the course of a controlled adjustment of the foil guide assembly of the instrument (radial movement), the foil or the foil segments slide(s) on each other due to its/their pretension (inherent elasticity), so that the diameter of the foil assembly can be increased or decreased as a whole.

According to one aspect of the invention, the punch along with its circular or essentially annular blade advances toward the die or an anvil, as with bone punch.

As an alternative to this, both the punch unit and the die unit may comprise a foil blade according to the invention. In this case, their foil guides or guiding assemblies may be designed such that the blades of the punch unit and the die unit each have different cutting diameters such that the two blades move past each other or perform a shearing motion or overlap in the axial direction. This improves the cutting performance. It is also conceivable that the two blades directly hit each other.

In order to facilitate the manipulation of the cutting instrument according to the invention for the surgeon and to ensure that the punch and the die as well as the cooperating blades always exhibit the correct width or correct difference in diameter, the width-adjustable guiding assembly of the punch unit and the width-adjustable guiding assembly of the die unit may be coupled to each other. The synchronous and analog width adjustment of said two units may be carried out in particular via a corresponding mechanical adjustment system and via a handpiece or a motor-powered device on the proximal end of the tool shaft.

According to one aspect of the invention, the supporting arms are spring-biased in the radial outward direction via one or several springs. These springs serve as an energy storage means for the spreading mechanism of the cutting tool. If the supporting arms are released, they will spread out by themselves due to the spring-induced pretension until they come into contact with the aortic inner wall which forms a kind of stop for the automatic spreading mechanism. The radial force of the supporting arms can also be adjusted via the spring-induced pretensioning. The supporting arms can be retracted again via a retraction mechanism.

In order to avoid a migration of the artificial heart valve in the best possible way, it is advantageous if the natural valve is not severed exactly at the aortic inner wall, but if there remains a constant attachment fixing the artificial valve in the axial direction. This is why the foil guide can be provided with a spacer or the foil in the guiding assembly can be guided at a certain distance radially within the outer dimension of the guiding assembly, so that it is ensured that the aortic wall is not impaired during punching. According to one aspect of the invention, it is possible that only the outer diameter of the guiding assembly is larger than the diameter of the annular blade by a defined predetermined distance. The radially raised or spread foil guides allow for the stretching of the aortic inner wall, whereas the blades provided so as to be further radially inside sever the aortic valve.

As the outer dimensions of the cutting unit are essentially determined by the guiding assembly, it is of advantage if the guiding assembly can be made flush with the tool shaft and the annular blade formed by the at least one foil can be reduced essentially to the diameter of the tool shaft. This allows the cutting unit to pass through the aortic valve, without scratching off or loosening any chalky plaque.

According to one aspect of the invention, the guiding assembly may be formed by several radially adjustable supporting arms distributed in the circumferential direction and coupled to each other, which can be parallel to the tool shaft axis via a parallelogram-type mechanic system, so that the foils are always aligned and guided so as to be axially parallel or parallel to the punching axis.

By means of two joint rods, the guiding arms are each articulated on two tool shaft components which can be moved axially relative to each other. Due to the axial displacement of the two tool shaft components, the guiding arms are raised radially outwards or pulled radially inwards via the joint rods. This conversion of an axial movement of a tool shaft drive into a radial movement of the guiding arms cannot only be handled and adjusted in a simple manner, but is also very space-saving.

According to one aspect of the invention, the number of the foils is equal to the number of the guiding arms. Here, the foil lengths are larger than the circular arc portion between two guiding arms with the largest adjustable cutting diameter.

According to one aspect, the guiding assembly comprises at least four radially adjustable guiding arms uniformly distributed in the circumferential direction. This is why the foils having the tendency to move radially outward are radially supported at least at four points.

Further, each foil may be firmly connected to a foil end on a corresponding guiding arm, preferably in a substance-to-substance bond. This ensures that the foil maintains its circumferential position or its relative position with respect to neighboring foils. On the other hand, it is ensured that the foil is fastened to the tool and cannot fall out of the guide, but without impeding the bending of the foil and the sliding of the foils during coiling and unrolling.

In order to reduce the sliding resistance between the foils or their overlapping sections for facilitating the process of coiling and unrolling the foils, anti-friction platelets or an anti-friction layer may be interposed between the foils. As an alternative or in addition, the corresponding foil surfaces sliding on each other (or at least portions of these) can be provided with an anti-friction coating.

According to one aspect of the invention, the foils in the width-adjustable foil guide may be supported in the radial direction only from outside. That is to say, the bent foils due to their inherent elasticity automatically follow a width adjustment of the guiding arms in the radially outward direction. This is advantageous in particular if the instrument is to be adjusted during the surgical procedure only in one direction, i.e. if the cutting unit is only to be enlarged from a compacted initial position to the diameter matching with the aortic diameter. In this case, the initially rolled-up foil follows the expansion of the foil guide without any further ado.

Alternatively, the foils may be received in axial grooves or slits provided on end faces of the guiding arms such that they protrude from these in the axial direction at least by the cutting depth which is to be expected. In these axial grooves, said foils are axially supported on the bottom of the groove and have their radially inner and outer sides supported by groove flanks. Said grooves are provided with such a dimension in the radial direction so that they are able to receive several foil layers in the compacted initial position. In the stretched state, there will be a larger radial clearance of the foils within the grooves. This gap, however, is basically not that important as the foils push outward by themselves and compensate for the gap.

However, in order to positively ensure that the foils do not tilt and do not swerve in the radial direction in the presence of an axial load, a gap compensation means may be provided which adapts or minimizes the distance between the foil layers and the groove walls depending on the decoiling state or the width adjustment. The gap compensation means may also be implemented in the form of a clamping or tensioning means bracing or clamping the foil in the axial grooves in the radial direction prior to the cutting process.

According to an aspect of the invention, the gap compensation means or the clamping or tensioning means may be a resilient element arranged in the axial groove and pressing the foil or its foil layers against one of the groove's inner walls, preferably against the radially outer inner wall of the groove. The pressing force of the resilient element may be dimensioned such that it permits, on the one hand, the sliding of the foil layers for coiling and decoiling the foils in the circumferential direction, but on the other hand prevents a radial spreading or tilting of the foils within the groove.

Instead of a resilient element within the groove, the clamping or tensioning means may be designed such that at least one of the groove walls can be repositioned in the radial direction and is capable of compensating for the gap generated during uncoiling the foils. In a preferred embodiment, the radially inner groove wall is repositioned radially outward. During the coiling process, it gives way in a corresponding manner towards the inside. The repositioning of the groove wall may also be realized by a spring element.

The clamping or tensioning means may also be implemented by a brake shoe system which releases the foils for width adjustment and can be activated immediately before the cutting process, e.g. by means of the handpiece.

In order to ensure that the (metal) foils are always in a tight contact, so that the foil in the cutting unit and the foil in the die unit can telescope during the punching or cutting process without touching the other foil, the resistive force can be reduced by a corresponding shape of the foil ends. To this end, at least one foil end may be slanted or pointed or rounded.

In order to further enhance the cutting performance, the punch unit and/or the die unit may perform a screw-like movement or a predetermined superimposed axial and rotational movement during the punching process. This may be achieved, for instance, by corresponding slotted guides provided in the tool shaft and forcing the punch unit and/or die unit to perform a rotary motion if they axially move toward each other in the cutting process.

According to an aspect of the invention, an elastic fine-mesh net may be laid over the foil guides or supporting arms, said net following the adjustment of the blade diameter and forming a closed space during the punching process, in which the severed aortic valves can be collected and safely recovered.

Depending on the case of application, it may be advantageous or necessary if the distal part of the punch-die assembly or the portion of the tool shaft according to the invention located behind the aortic valve is not pulled out along with the instrument after the aortic valve resection, but can be detached from the instrument and recovered in some other way. It is also possible to separately insert the two cutting tools before the resection of the aorta and to connect them to each other within the body in the so-called rendezvous procedure. This is why—according to one aspect of the invention—the punch unit and the die unit may be detachably coupled to each other, so that the distal part of them can be coupled to or uncoupled from the tool shaft prior to or after resection of the aortic valve.

According to one aspect of the invention, the instrument shaft can be designed to be flexible. In this case, the instrument shaft comprises a central and axial through-hole for receiving a guide wire. The guide wire may have provided its distal end with an expandable positioning device such as a spreading mechanism, a balloon or the like, in order to position and fix the guide wire in the vicinity of the aortic valve. The flexible instrument shaft can then be guided to the aortic valve via the guide wire.

BRIEF DESCRIPTION OF THE DRAWING FIGURES

The present invention is illustrated in more detail on the basis of attached drawings in which:

FIG. 4 is a cross-sectional view of the instrument shaft comprising a folded cutting unit (without foil blade) according to the first embodiment;

DETAILED DESCRIPTION

Figure 1:
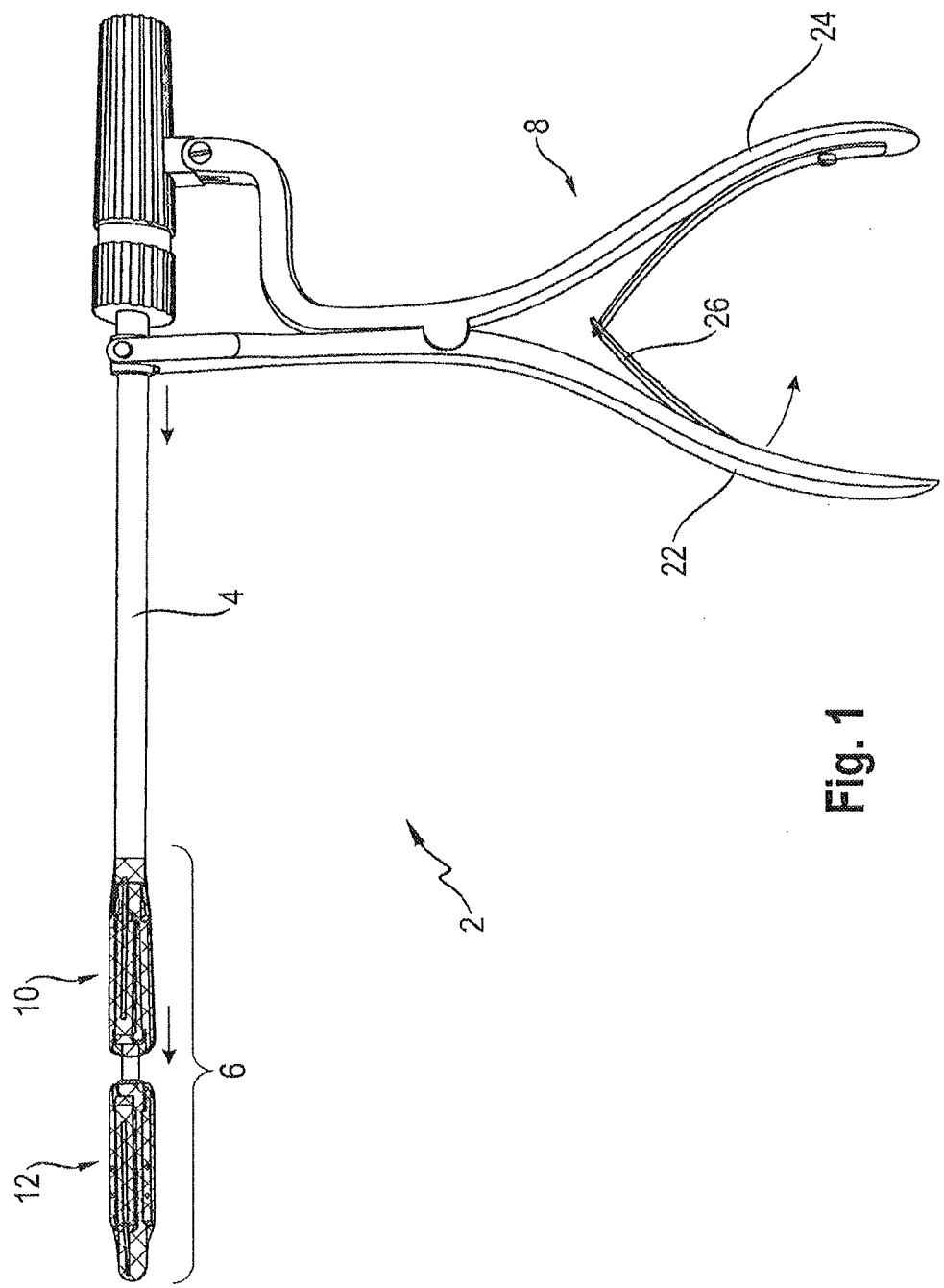
FIG. 1 shows a cutting instrument of the invention according to a first embodiment of the invention.
Figure 2:
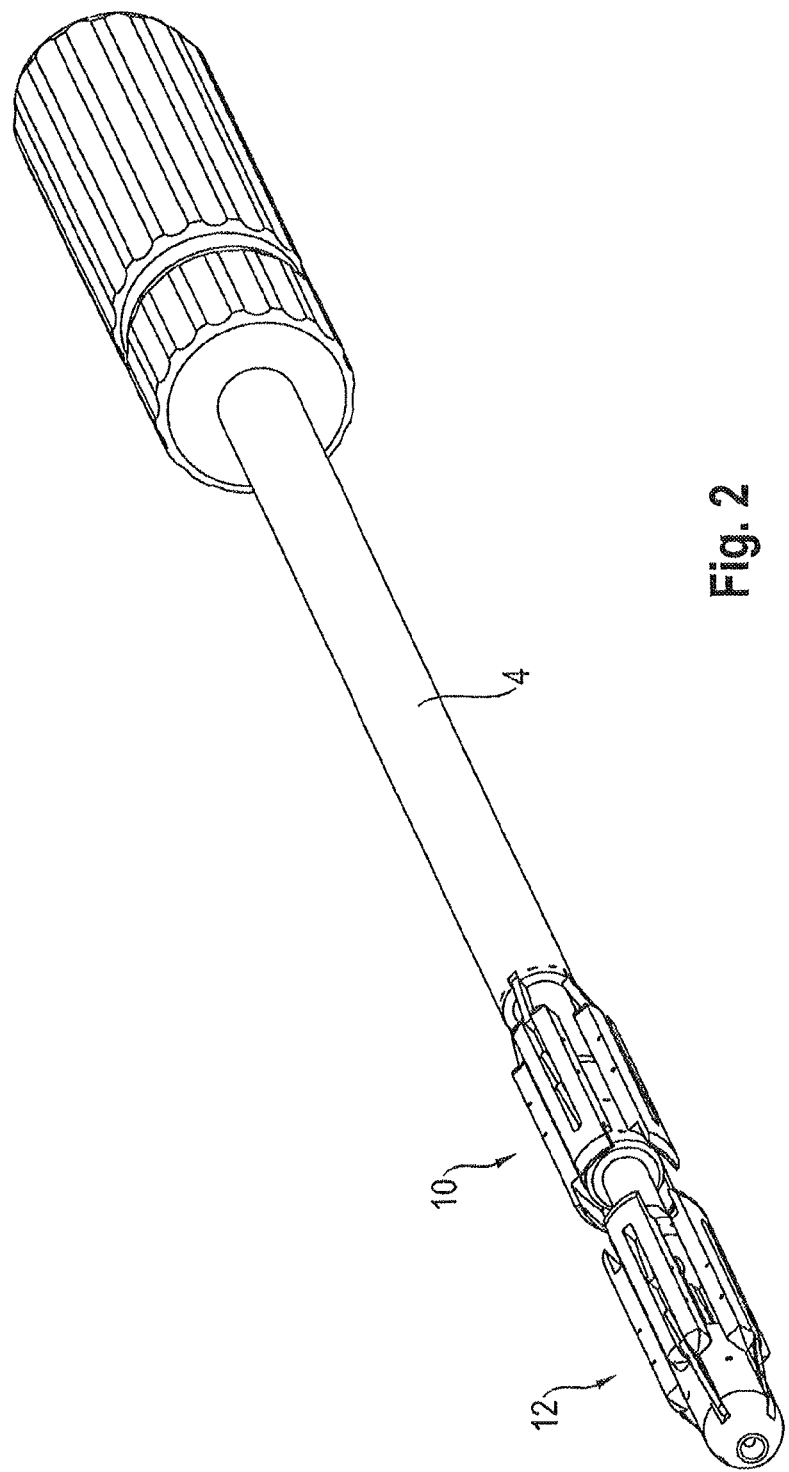
FIG. 2 is a perspective view of the instrument shaft comprising a folded cutting unit (without foil blade) according to the first embodiment.

FIG. 1 shows a cutting instrument 2 designed according to the invention and having its distal end of a tool shaft 4 provided with a cutting unit 6 which can be actuated via a handpiece 8 arranged on the proximal end of the tool shaft 4. The shaft 4 may be rigid or flexible; if necessary, it may be able to be manipulated via the handpiece 8. The cutting unit 6 is essentially formed as a punch-die assembly and consists of two cutting tools 10 and 12 which are axially arranged on the tool shaft 4 and can be moved toward each other or apart from each other via the handpiece 8. To be more precise, the proximal cutting tool 10 in the illustrated example acts as a movable punch unit and the distal cutting tool 12 acts as a static die unit. It goes without saying that—in an alternative design—the distal cutting tool 12 is movable toward the proximal cutting tool 10 or both are movable relative to each other.

The cutting tools 10, 12 each comprise a blade 14 whose construction and way of functioning is described in more detail below.

The handpiece 8 comprises two ergonomically shaped, hinged handles 22 and 24 which are biased into an initial position via a spring 26. In the initial position, the cutting tools 10, 12 are spaced from each other.

The tool shaft 4 is of a multi-piece design and comprises a first shaft unit 28 which is connected on the one hand to the punch 10 and, on the other hand, is connected in articulated fashion to one of the handles 22, 24, namely to the handle 22. The shaft unit 28 can be moved in axial direction relative to a second shaft unit 30 which is connected on the one hand to the die 10 and, on the other hand, is connected in articulated fashion to the other of the two handles 22, 24, i.e. handle 24. The user of the instrument 2 may grip the handles 22 and 24 with his fingers and ball of the hand and actuate them against the spring force of the spring 26, so that the punch 10 is moved axially toward the die 12 and punches or severs any tissue therebetween.

Both the cutting tool 10 acting as a punch and cutting tool 12 acting as a die can be adjusted in width via an actuating mechanism whose construction and way of functioning is illustrated in detail below; here, FIG. 2 to FIG. 5 show in a simplified illustration only the tool shaft 4 without the handpiece 8.

Figure 3:
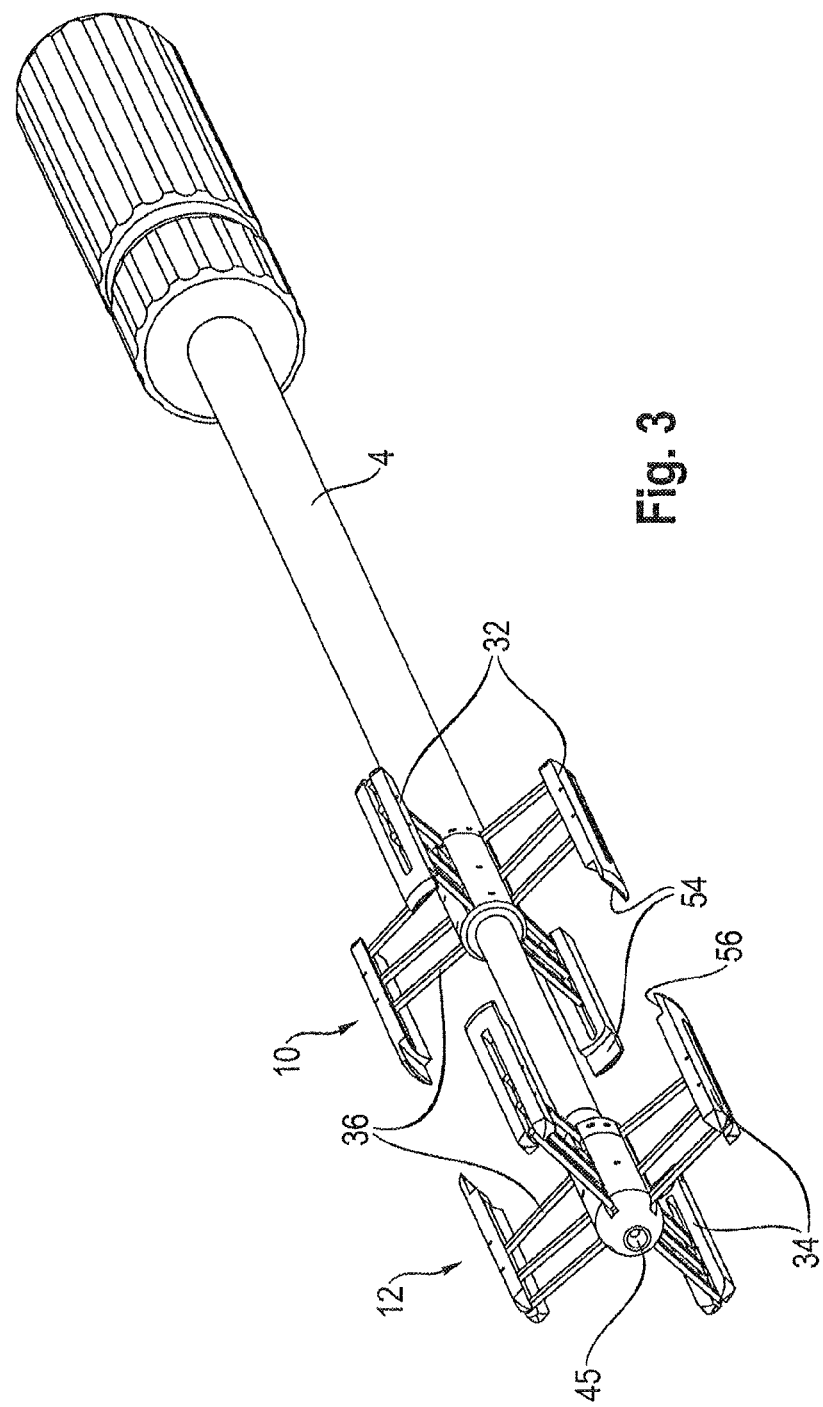
FIG. 3 is a perspective view of the instrument shaft comprising a spread cutting unit (without foil blade) according to the first embodiment.
Figure 5:
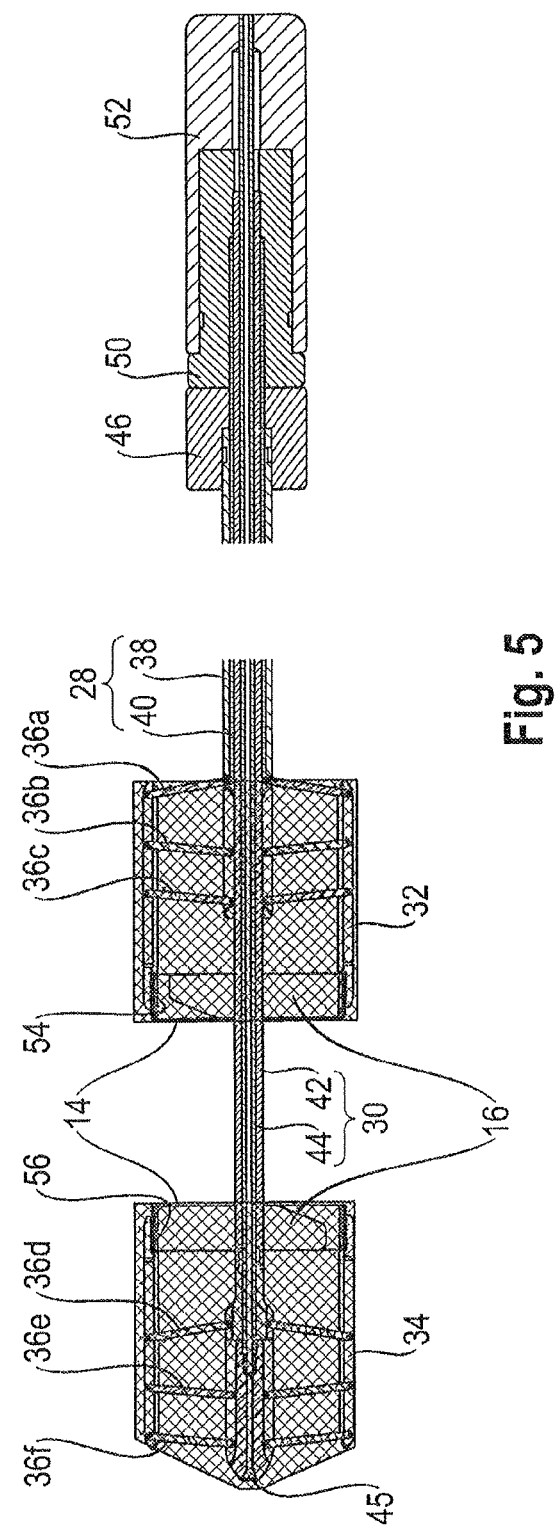
FIG. 5 is a cross-sectional view of the instrument shaft comprising a spread cutting unit (including foil blade) according to the first embodiment.

The cutting unit 6 or the cutting tools 10 and 12 can be continuously adjusted between a packed or folded position in which the cutting tools 10 and 12 have their minimum diameter (see FIG. 2 and FIG. 4), and a spread position in which the cutting tools 10 and 12 occupy their maximum diameter (see FIG. 3 and FIG. 5).

Each cutting tool 10 and 12 comprises several (in the present example four) guides or guiding arms 32 and 34 which are uniformly distributed in the circumferential direction and extend in the axial direction or parallel to the tool shaft 4. These guiding arms 32, 34 are each guided via several articulated arms 36 on the tool shaft 4 and can be adjusted via said articulated arms 36 radially to the tool shaft 4, i.e. can be spread towards outside or collapsed inwards.

The first shaft unit 28 (see FIG. 5) of the first cutting tool 10 consists of an exterior hollow shaft 38 and a second interior hollow shaft 40 which can be axially moved within the former. Among the articulated arms 36 of the corresponding guiding arm 32, one articulated arm 36a is hinged to the exterior hollow shaft 38, whereas two other articulated arms 36b, 36c are hinged to the interior hollow shaft 40. The hinges via which the articulated arms 36 are connected to the guiding arms 32 and the exterior hollow shaft 38 or interior hollow shaft 40 define a parallelogram. Said parallelogram-type mechanic system ensures that the guiding arms 32 during width adjustment are always kept in parallel alignment with the tool shaft 4 if the two hollow shafts 38, 40 are moved apart or into each other and, in so doing, push the guiding arms radially outward or pull them inward via the articulated arms 36 hinged thereon (cf. FIG. 2 and FIG. 3). The three articulated arms 36a, 36b, 36c clearly define the position and the orientation of the guiding arms 32, so that the guiding arms 32 do not tilt relative to one another during a relative displacement of the shafts 38, 40.

The second shaft unit 30 of the second cutting tool 12 is constructed in the same way as the first shaft unit 28 and likewise comprises two shaft pieces which can be axially moved relative to each other, i.e. an exterior hollow shaft 42 and a shaft 44 which is axially guided and can be moved therein. It is to be noted that the second shaft unit 30 is received within the first shaft unit 28 and can be axially moved therein. Also, the second shaft unit 30 comprises the parallelogram-type mechanic system which has been described in detail above and displaces (via the shaft pieces 42, 44 which can be shifted relative to each other) the guiding arms 34 parallel to the shaft pieces 42, 44 and the tool shaft 4. Here, one articulated arm 36d is connected to the exterior hollow shaft 42 and two articulated arms 36e, 36f are connected to the interior shaft 44.

The distal end of the instrument shaft 4 is provided with a central axial hole 45 (see FIGS. 3 and 5) for a guide wire which extends throughout the entire instrument shaft 4. The cutting unit 6 can be guided to the aortic valve by means of a guide wire which has been positioned near the aortic valve and inserted in the instrument shaft.

In the present example, the width adjustment of the two cutting tools 10 and 12 is mechanically coupled to each other, so that their diameters are enlarged or decreased collectively and in analog fashion.

The relative movement of the two shaft pieces 38, 40 associated to the first shaft unit 28 and of the two shaft pieces 42, 44 associated to the second shaft unit 30 is effected by a screw drive which is actuated via a rotary knob 46 arranged on the proximal end of the tool shaft 4. Any rotary movement which is input at this place is converted into a translational relative displacement of the respective shaft pieces 38, 40, 42, 44 with respect to one another. Said mechanic system required for width adjustment is released if the handles 22, 24 are in their initial position, and are blocked if the handles 22, 24 are actuated for cutting purposes.

FIG. 4 shows a cross-sectional view of the tool shaft 4 without the handpiece 8. The rotary knob 46 is axially coupled to the exterior hollow shaft 38 of the first shaft unit 28 and can be rotated relative to it. The rotary knob 46 is also in threaded engagement with the interior hollow shaft 40 of the first shaft unit 28, so that a rotary motion of the rotary knob 46 results in an axial relative displacement of the two hollow shafts 38, 40, without turning these relative to each other.

The rotary knob 46 is coupled in a torque-proof manner to a rotary piece 50 via an eccentrically arranged axial pin 48, and said rotary piece is in turn axially coupled to a shaft end piece 52 and can be rotated relative to it. Said shaft end piece 52 is firmly connected to the interior shaft 44 of the second shaft unit 30, whereas the rotary piece 50 is in threaded engagement with the exterior hollow shaft 42 of the second shaft unit 30. Thus, any rotation of the rotary knob 46 does not only result in a relative displacement of the shaft parts 38, 40 of the first shaft unit 28 and the concomitant width adjustment of the first cutting tool 10, but—via the coupling to the rotary piece 50—also to a relative displacement of the shaft parts 42, 44 of the second shaft unit 30 and a concomitant width adjustment of the second cutting tool 12. It is due to said coupling that the shaft units 28, 30 and cutting tools 10, 12 are adjusted in width in synchronous manner.

In the following, the construction and the width adjustment of the annular blade 14 will be explained.

The annular blade 14 is not formed by a static annular cutting element, but by a thin and narrow, flexible foil band 16 which may be made of metal or a metal alloy, in particular of Nitinol, or of any other suitable elastically bendable material. The foil 16 or at least its edge 18 should have such a small thickness that the edge 18 achieves a cutting effect for human tissue in the presence of a certain pressure and optionally an additional rotary motion. For sharpening the edge 18, it may be additionally provided with a bevel.

Whereas the elongated foil band 16 is elastically bendable in the longitudinal direction, it is comparably stiff in the transverse direction. If the foil 16 is bent to a ring such that the foil ends overlap and—as illustrated in FIG. 5—is inserted in corresponding seats 54 and 56 of the two cutting tools 10, 12, the rigidity of the foil 16 will be increased to such an extent that it can be used as a blade. Due to its elastically bendable pretension, the overlapping sections 20 of the foil 16 tightly rest against each other, so that the edges 18 of the foil 16 form an essentially closed and ring-shaped annular blade 14.

The seat 54 and 56 are located on opposing axial ends of the guiding arms 32 and 34. The width of the foils 16 is sized such that the foils 16 axially protrude from the seats 54, 56 by some extent; to be more precise, by the expected cutting depth.

These seats 54, 56 essentially are radial shoulders in the guiding arms 32, 34, supporting the foil 16 only in the axial direction and only from radially outside. Due to the inherent elasticity of the metal foil 16, it strives to return to its initial state after deformation. Due to said restoring force, the foil 16 is clamped in a force-fit manner in the seats 54, 56 the four guiding arms 32, 34 which are uniformly distributed in the circumferential direction.

Figure 6:
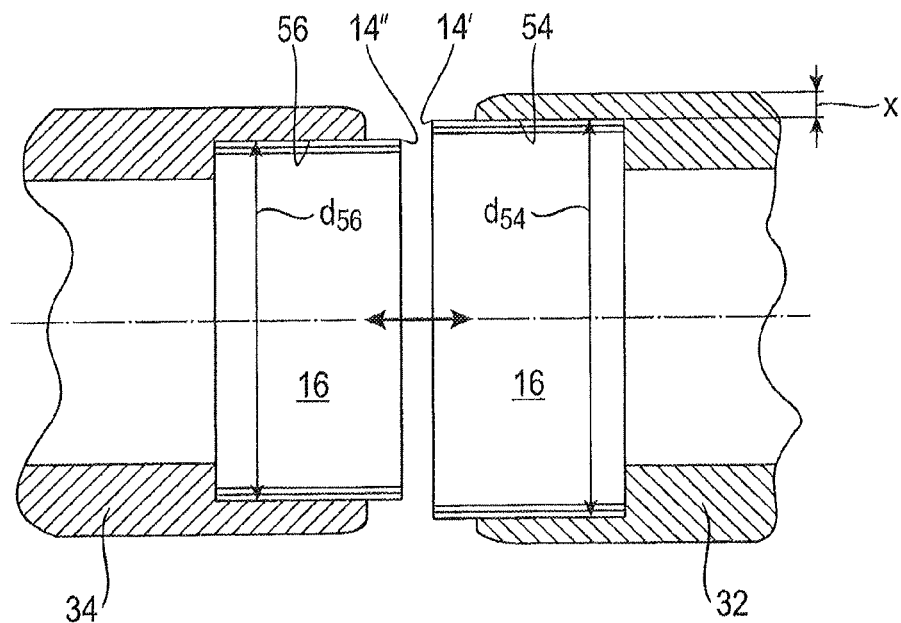
FIG. 6 is an enlarged cross-sectional detail view of the foil guides of the cutting unit according to the first embodiment.

The seats or shoulders 54, 56 in the guiding arms 32, 34 of the punch 10 and the die 12 may differ and have different radial depths or different diameters $d_{54}$, $d_{56}$, as illustrated in the cross-sectional view in FIG. 6. Said difference in diameter in the radial support area of the metal foils 16 results in a difference in diameter in the annular blade 14 formed by the foils 16. Said difference in diameter is selected such that the annular blade 14 of the punch 10 and the annular blade 14 of the die perform a shearing motion or can be moved past each other.

Figure 8:
FIG. 8 shows an unwrapped foil blade in the initial state.

In order to ensure that the metal foil segments 16 always have a tight contact to each other and to guarantee that the annular blade 14 of the punch 10 is able to penetrate into the die 12 or its annular blade 14 during the punching process without any collision between them, the foil ends are provided with a corresponding shape so as to lower the resisting moment. For this purpose, the end portions of the foils are slanted and optionally rounded, in particular in the insertion direction (see FIG. 8).

Figure 7:
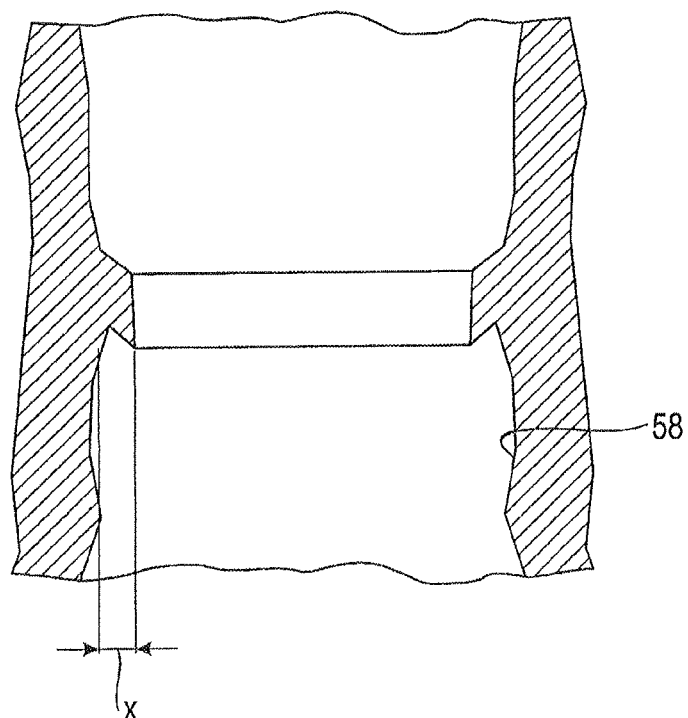
FIG. 7 is an enlarged cross-sectional detail view of the aorta after an aortic valve resection.

Further, the seats 54, 56 are not disposed immediately in the outer area of the guiding arms 32, 34, but are arranged further inwards in radial direction by a certain distance x, so that during the cutting process the aortic wall 58 is not affected during punching, on the one hand, and the natural aortic valve is not severed exactly at the aortic inner wall 58, on the other hand, but a constant attachment x remains for axially fixing the artificial valve (see FIG. 7). The exterior portions of the guiding arms 32, 34 serve, so to speak, as a spacer for supporting and stretching the aortic inner wall 58.

As the guiding arms 32, 34 are moved radially outside in a parallel manner via a parallelogram-type mechanic system, as already illustrated above, the seats 54, 56 and the foils 16 received therein are always aligned and guided in parallel to the punching axis in order to achieve their maximum cutting action with their edge 18.

The diameter of the annular blade 14 formed by the foil 16 can be continuously adjusted by radially adjusting the guiding arms 32, 34; in doing so, the overlapping foils 16 slide on each other.

If the width of the guiding arms 32, 34 is enlarged, for example, the seats 54, 56 move radially outward and the foils 16 clamped therein follow the seats 54, 56 in automatic fashion due to their elastically bendable pretension. The foils 16 slide on their overlapping sections 20 with respect to each other. The maximal width adjustment is limited by the length of the foil 16 and can be carried out only as long as the foil ends still overlap.

If, however, the width of the guiding arms 32, 34 is reduced, the seats 54, 56 move radially inward and the foils 16 clamped therein are further pushed in the inward direction, whereby the foil ends slide on each other and the foil 16 is coiled more and more.

For adjusting the width of the foils 16, it is required that they be able to slide in the circumferential direction so as to unroll or curl up; hence, they need a specific degree of freedom in the circumferential direction. However, in order to avoid the foils 16 from slipping or falling out of the guiding arms 32, 34 in the axial direction or in order to prevent the foils 16 from always having the same spacing in the circumferential direction, an end or a middle portion of the foil bands 16 may be glued, soldered or fastened to the corresponding guiding arm 32, 34 in any other way, whereas the other end remains freely movable. If one foil is used, it is preferred that a foil end is fixed, and if several foil segments are used, it is preferred that a middle portion of the foil segment is fixed in each case.

Figure 9A:
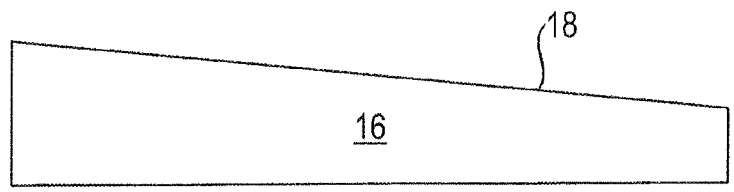
FIGS. 9A to 9D show various edge geometries of the foil blade.
Figure 9B:
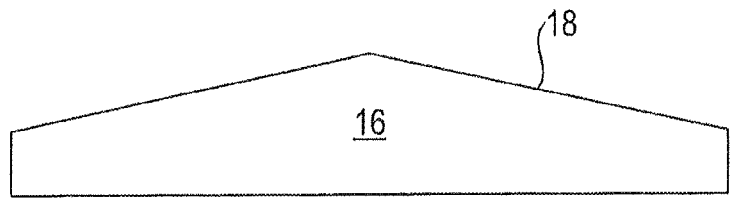
Figure 9C:
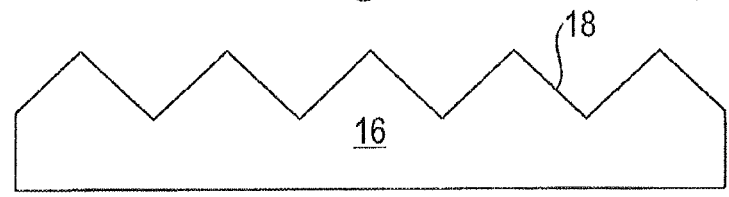
Figure 9D:
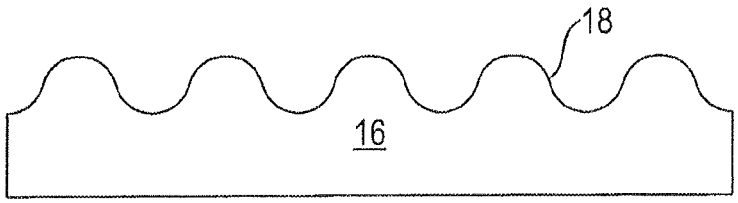

In order to prevent that the entire blade 14 comes into contact with the tissue at the same time, the foil 16 may comprise different blade geometries including an oblique, serrated or wavy cutting edge 18 (see FIG. 9A to 9B), for example, in order to reduce the cutting or punching forces.

In the following, a second embodiment of the invention will be described, with which an identical cutting instrument is used; the foil blade, however, is not a single foil, but several foil segments 16 arranged in the circumferential direction are used.

Figure 10:
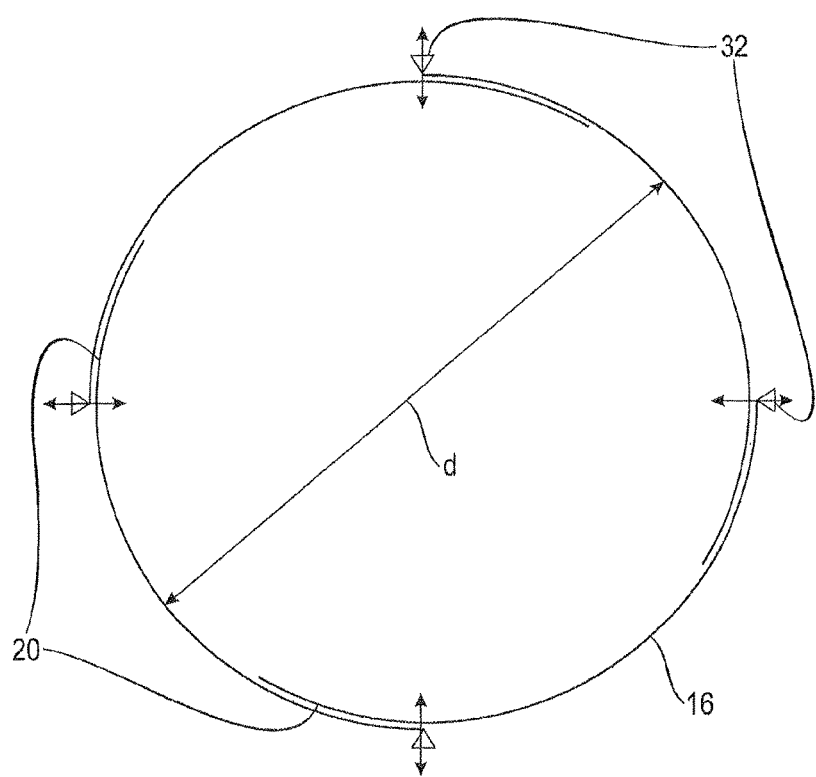
FIG. 10 is a schematic view of a foil blade, formed by several foils, according to a second embodiment and having a medium cutting diameter.

As is schematically and exemplarily illustrated in FIG. 10 for a cutting tool (punch or die), several foils 16 (which are shorter as compared to the first embodiment) are arranged in their longitudinal extension one after the other such that they overlap in alternating fashion inside and outside. This foil assembly will be bent so as to result in a circular ring, so that the first and the last foil 16 overlap as well; subsequently—like in the first embodiment—it is inserted in corresponding seats 54 and 56, respectively, which are formed on an axial end of the guiding arms 32 and 34. Due to their elastically bendable pretension, the overlapping sections 20 of the foils snuggle into each other in tight fashion, so that the edges 18 of the assembly of the four foils 16 form an essentially closed and circular annular blade 14.

Due to the inherent elasticity of the metal foil segments 16, these also have the tendency to return to their initial state after deformation. This restoring force has the effect that the foils 16 are clamped in force-fitting manner in the seats 54, 56 of the four guiding arms 32, 34 uniformly distributed in the circumferential direction.

Figure 11:
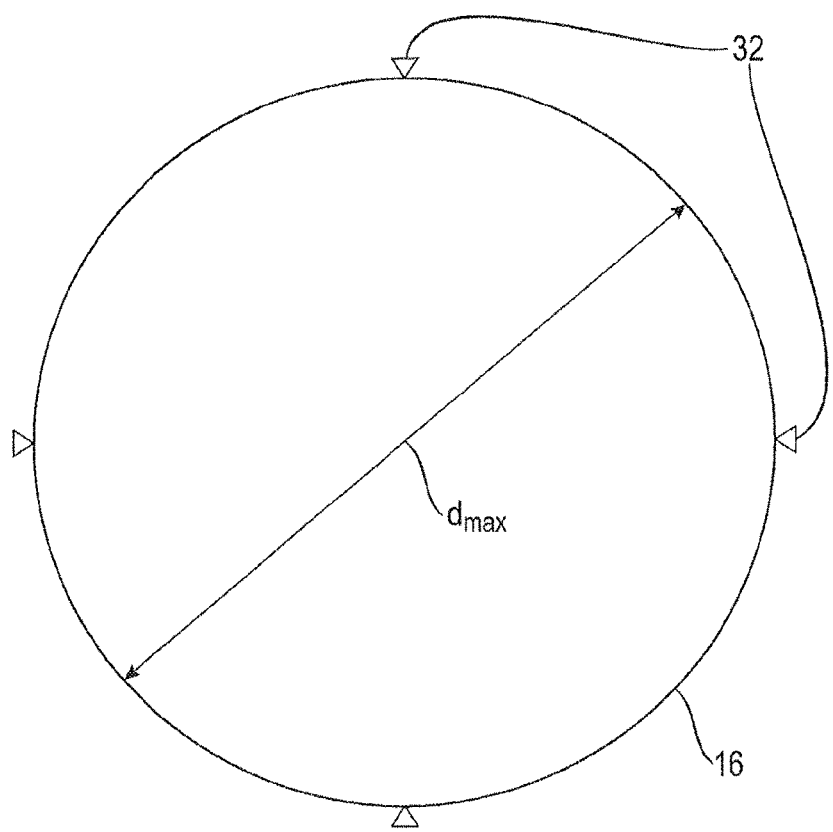
FIG. 11 is a schematic view of a foil blade, formed by several foils, according to a second embodiment and having a maximum cutting diameter.

As described in detail above, the diameter of the annular blade 14 formed by the foil assembly can be continuously adjusted by a radial adjustment of the guiding arms 32, 34; in this process, the neighboring and overlapping foils 16 slide in each case so as to curl up or unroll. Apart from the guiding arms 32, the foil segments are mutually supported on the overlapping sections 20. The maximum width adjustment is dictated by the number of the foils 16 and their respective length and is possible only up to a diameter with which neighboring foils 16 still overlap. The limit for increasing the diameter will be reached at the latest when the metal foils segments do not have any guidance among each other (see FIG. 11).

If, however, the width of the guiding arms 32, 34 is reduced, the seats 54, 56 move radially inward and the foils clamped therein are pushed further inward and bent to a still higher extent. The overlapping foils 16 curl up even more and the overlapping sections 20 become even larger.

Figure 12:
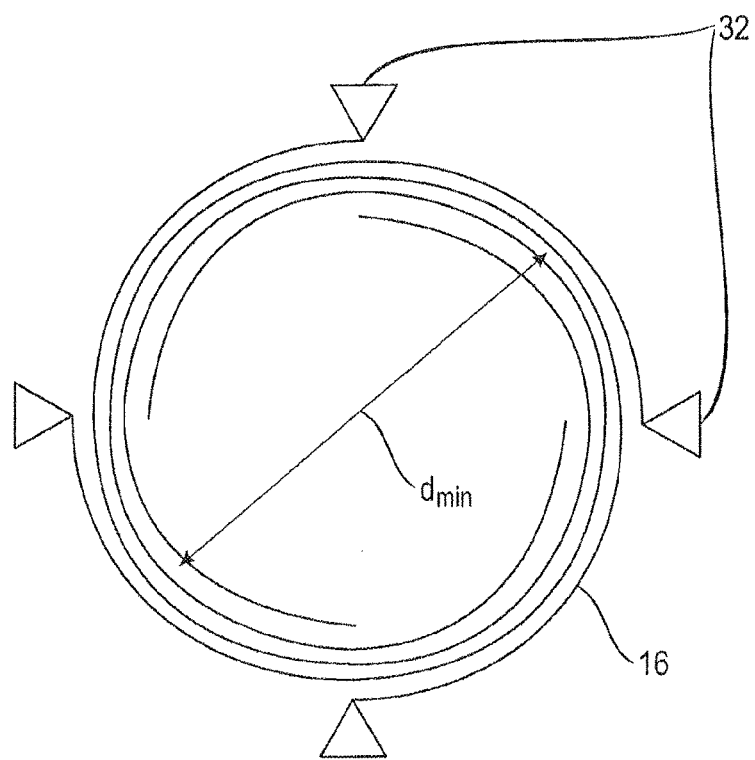
FIG. 12 is a schematic view of a foil blade, formed by several foils, according to a second embodiment and having a minimum cutting diameter.

Even if the foils 16 can be rolled up in an inward direction and pushed into each other to almost any extent, a certain limit is reached if each foil 16 has been bent essentially by 360° and 4 layers of superimposed foil segments 16 are present everywhere (see FIG. 12).

For adjusting the width of the foils 16, it is required that they be able to slide in the circumferential direction so as to unroll or curl up; hence, they need a specific degree of freedom in the circumferential direction. However, in order to avoid the foils from slipping or falling out of the guiding arms in the axial direction or in order to prevent the foils from always having the same spacing in the circumferential direction, an end of the metal foil bands may be glued, soldered or fastened to the corresponding guiding arm 32, 34 in any other way, whereas the other end remains freely movable.

Figure 13:
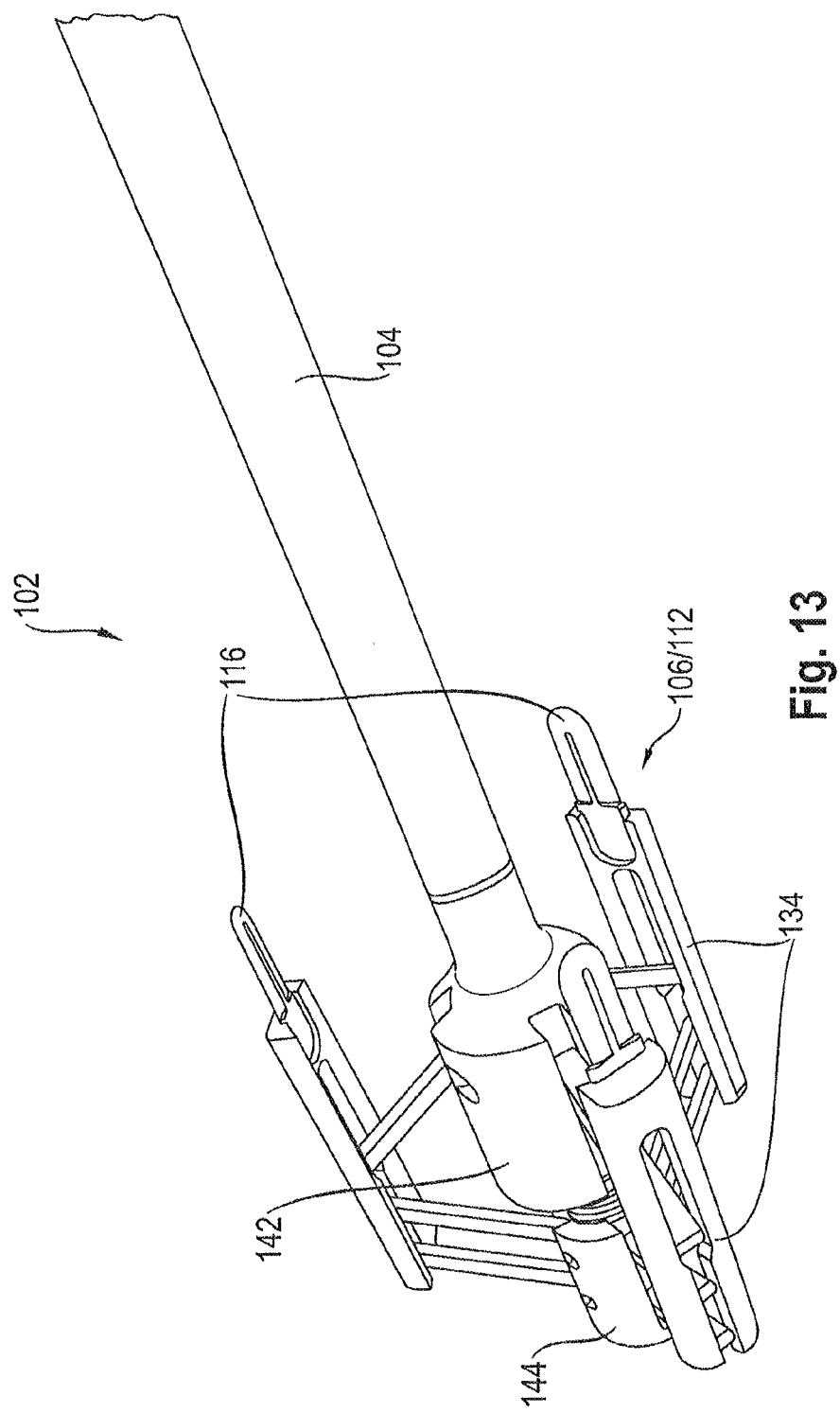
FIG. 13 is a perspective partial view of a cutting instrument according to a third embodiment of the invention.
Figure 14:
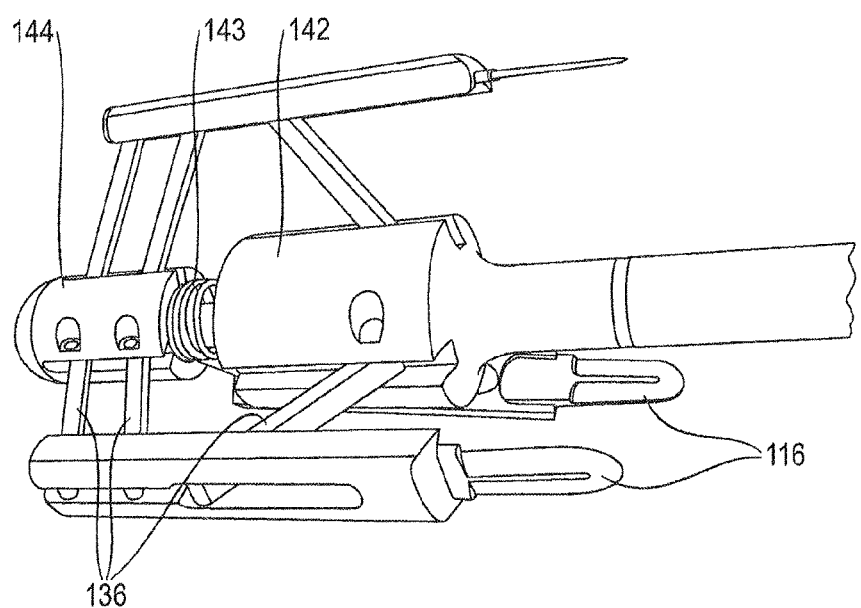
FIG. 14 is an enlarged view of the cutting unit of the cutting instrument according to the third embodiment of the invention.

FIG. 13 shows a distal portion of a cutting instrument 102 according to a third embodiment of the invention. This cutting instrument 102 is very similar to the first two embodiments regarding the construction and its mechanical system; however, it does not comprise a punch-die assembly on the distal end of a tool shaft 104, but a cutting tool 112 which can also be adjusted in width via an actuating mechanism and can be rotated around the instrument shaft axis. The blade is not formed by a foil blade, but by individual cutting blades 116 which are each detachably fastened to a distal axial end of supporting arms 134, e.g. are inserted in an axial slit, or are firmly fastened thereto, and extend in the axial direction or the direction parallel to the shaft and are provided with blades 116 in two circumferential directions. The blades 116 are again arranged so as to be arranged radially further inward than the outer surfaces of the supporting arms 134 by the distance x. The cutting blades 116 extend contrary to the insertion direction of the instrument 102, so that they do not act as a bayonet and injure tissue during insertion. When the cutting tools 110 are rotated in any direction, the three cutting blades 116 make a circular cut. Similar to the first two embodiments, the supporting arms 134 can be shifted via an actuating mechanism in parallel to the shaft axis, whereby the cutting diameter of the cutting blades 116 can be adjusted. The actuating mechanism is essentially identical to the first two embodiments, so that also in this case a (not illustrated) rotary knob on the distal end of the instrument shaft allows for the actuation of a shaft unit with a parallelogram-type mechanical system described in detail above. A difference to the first two embodiments lies in the fact that a spring 143 is arranged between the shafts, 142, 144 which can be shifted relative to each other and bring about the width adjustment, said spring biasing the two shafts 142, 144 in a direction of adjustment. As an alternative, the width adjustment may be achieved by means of a thread.

The function of the instrument 102 is very similar to that of the instrument 2. For inserting the instrument 102, the supporting arms 134 and the cutting blades 116 are pulled up to the tool shaft 104 as closely as possible. Subsequently, the instrument 102 is inserted in a transapical manner and the cutting tool 112 is guided centrally through the aortic valve opening. In a next step, the supporting arms 134 are spread by actuating the actuating mechanism so far until the supporting arms 134 rest against the aortic inner wall. In a screw-like movement, i.e. in a superimposed axial and rotational movement toward the distal end of the instrument shaft, the blades 116 make a resection on the aortic valve. This cutting motion may be performed by a handpiece provided on the distal end of the instrument shaft or can be effected in a motor-driven manner.

The present invention has been illustrated on the basis of preferred embodiments, but is not limited to these.

It is possible, for instance, to vary the number of the foil guides, foil segments and cutting blades. It makes sense, however, to select a number which is as large as possible, so that a good guidance of the metal foil segments is ensured.

As described above, the punch and the die move into each other by a certain travel and cut off any tissue between them. It is also conceivable, however, that the seats for the punch and the die are identical and both annular blades have the same diameter. Further, the cutting unit may also work like a bone punch; in this case, only one of the two tools comprises a blade and the other tool merely serves as an anvil.

It is also conceivable that an elastic fine-meshed net is laid over the foil guides, as is already indicated in FIG. 4 and FIG. 5. This net follows the adjustment of the punching diameter and forms a closed space during the punching process, in which the severed aortic valves can be collected and safely recovered. This also prevents any chalky particles from finding their way into the bloodstream. Moreover, the net maintains the blood flow during the punching process.

In the embodiment shown above, the foil blade is only provided with an external guide as the foil or the foil segments have the tendency to unroll and push radially outward. However, the foils may also be internally guided in addition. In a variant, the radial interior guide is repositionable in order to be able to compensate for a resultant gap in the foil guide and to tense up the foils for the cutting process, if necessary.

In a variation, the entire distal portion forming the base of the second cutting tool can be separately inserted and can be coupled to the instrument in the course of an intracorporeal rendezvous procedure or can be detached from the instrument after the successful cutting process via a mechanical system actuatable by the handpiece and otherwise recovered.

In a further variation, the two cutting tools—when brought together via the handpiece for cutting off the aortic valve—do not only perform a purely translational movement, but a combined translational and rotational movement or screw-like movement.

The invention claimed is:

1. A surgical cutting instrument for aortic valve resection, comprising a cutting unit arranged on a distal end of a tool shaft and comprising at least one mechanical cutting element for making a circular incision, the at least one mechanical cutting element configured to be continuously adapted to different aortic diameters by a radially movable actuating mechanism, wherein the actuating mechanism comprises one or more supporting arms or guiding arms distributed in a circumferential direction and supporting and guiding the at least one mechanical cutting element, the actuating mechanism designed such that the one or more supporting arms or guiding arms can be expanded and retracted parallel to an axis of the tool shaft so that the one or more supporting arms or guiding arms and the at least one mechanical cutting element remain in a parallel alignment relative to the axis of the tool shaft throughout an entire adjustment range, wherein the tool shaft comprises a first tool shaft component and a second tool shaft component, and the one or more supporting arms or guiding arms are each connected to the first tool shaft component by at least a first joint rod and are each connected to the second tool shaft component by at least a second joint rod, the first and second tool shaft components being axially movable relative to each other such that an axial movement of the first and second tool shaft components is converted, via the first and second joint rods, into a radial movement of the one or more supporting arms or guiding arms.

2. The surgical cutting instrument according to claim 1 comprising a tool handle arranged on the proximal end of the tool shaft and a rotary knob, manually actuatable handle piece which is coupled to the actuating mechanism to manually adjust the width of the cutting element which is already in a functional cutting position.

3. The surgical cutting instrument according to claim 1, wherein the cutting unit comprises a punch-die assembly, the punch-die assembly comprising a punch unit and a die unit being movable at least in an axial direction relative to the punch unit, the punch-die assembly comprising at least one foil that is thin, elastically bendable, and annularly bent, the at least one foil overlapping itself in the circumferential direction in spiral fashion and being made of metal or metal alloy comprising foil layers, the foil layers having a mutual flat contact such that a front edge of the at least one foil in a spiraled state forms a single, common and essentially annular blade whose diameter can be continuously adapted to different aortic diameters by curling up or unrolling the foil.

4. The surgical cutting instrument according to claim 3, wherein the at least one foil comprises an assembly of several thin, elastically bendable, and annularly bent foils which overlap in the circumferential direction and are made of metal or metal alloy and have a mutual flat contact such that their edges form a single, common and essentially annular blade whose diameter can be continuously adapted to different aortic diameters by a relative movement of the foils in the circumferential direction.

5. The surgical cutting instrument according to claim 3, wherein the at least one foil is supported on an outside of at least one of the one or more supporting arms or guiding arms in the radial direction, and wherein the at least one of the one or more supporting arms or guiding arms is radially adjustable via the actuating mechanism, the at least one foil automatically following a width adjustment in a radially outward direction due to an inherent elasticity of the at least one foil.

6. The surgical cutting instrument according to claim 5, wherein the at least one foil comprises a plurality of foils, and the at least one of the one or more supporting arms or guiding arms comprises a plurality of supporting arms or guiding arms, and wherein a total number of said plurality of foils is equal to a total number of said plurality of supporting arms or guiding arms.

7. The surgical cutting instrument according to claim 5, wherein the at least one foil comprises a first foil on the punch unit and a second foil on the die unit, and wherein the blade of the at least one foil comprises a first blade on the first foil and a second blade on the second foil, the punch unit and the die unit each comprising a foil guide formed by at least one of the one or more supporting arms or guiding arms, wherein the foil guide of the punch unit comprises a first diameter and the foil guide of the die unit comprises a second diameter, wherein the first diameter and the second diameter differ such that the first and second blades move past each other or perform a shear movement.

8. The surgical cutting instrument according to claim 5, wherein the at least one of the one or more supporting arms or guiding arms comprises a fine-meshed, elastic net which follows the width adjustment and forms a closed space during a punching process, in which space the severed aortic valves can be collected and safely recovered.

9. The surgical cutting instrument according to claim 3, wherein the overall length of the at least one foil is, as a whole, longer than a circumference of a maximally adjustable cutting diameter.

10. The surgical cutting instrument according to claim 3, wherein the at least one foil comprises a slanted or tapered foil end.

11. The surgical cutting instrument according to claim 3, wherein the punch unit and the die unit are detachably coupled to each other and distal parts of the punch unit and the die unit can be coupled to or uncoupled from the tool shaft.

12. The surgical cutting instrument according to claim 1, wherein the cutting unit comprises a cutting tool which is rotatably supported around the tool shaft and comprises at least one cutting blade whose radial distance to the rotational axis can be continuously adjusted to different aortic diameters via the actuating mechanism.

13. The surgical cutting instrument according to claim 1, wherein the one or more supporting arms or guiding arms comprises a plurality of axially aligned guiding arms, which are coupled to each other and serve as foil guides or as cutting blade carriers, and can be shifted parallel to the axis of the tool shaft by the actuating mechanism by a parallelogram-type mechanic system.

14. The surgical cutting instrument according to claim 1, wherein the one or more supporting arms or guiding arms can be shifted parallel to the axis of the tool shaft by means of a parallelogram-type mechanic system.

15. A surgical cutting instrument for aortic valve resection, comprising a cutting unit arranged on a distal end of a tool shaft and comprising at least one mechanical cutting element for making a circular incision, the at least one mechanical cutting element configured to be continuously adapted to different aortic diameters by a radially movable actuating mechanism, wherein the actuating mechanism comprises one or more supporting arms or guiding arms distributed in a circumferential direction and supporting and guiding the at least one mechanical cutting element, the actuating mechanism designed such that the one or more supporting arms or guiding arms can be expanded and retracted parallel to an axis of the tool shaft so that the one or more supporting arms or guiding arms and the at least one mechanical cutting element remain in a parallel alignment relative to the axis of the tool shaft throughout an entire adjustment range, wherein the one or more supporting arms or guiding arms are each connected to the tool shaft via at least two joint rods, wherein each of the one or more supporting arms or guiding arms defines a parallelogram with the tool shaft and two joint rods.

16. The surgical cutting instrument according to claim 15 comprising a tool handle arranged on the proximal end of the tool shaft and a rotary knob, manually actuatable handle piece which is coupled to the actuating mechanism to manually adjust the width of the cutting element which is already in a functional cutting position.

17. The surgical cutting instrument according to claim 15, wherein the cutting unit comprises a punch-die assembly, the punch-die assembly comprising a punch unit and a die unit being movable at least in an axial direction relative to the punch unit, the punch-die assembly comprising at least one foil that is thin, elastically bendable, and annularly bent, the at least one foil overlapping itself in the circumferential direction in spiral fashion and being made of metal or metal alloy comprising foil layers, the foil layers having a mutual flat contact such that a front edge of the at least one foil in a spiraled state forms a single, common and essentially annular blade whose diameter can be continuously adapted to different aortic diameters by curling up or unrolling the foil.

18. The surgical cutting instrument according to claim 17, wherein the at least one foil comprises an assembly of several thin, elastically bendable, and annularly bent foils which overlap in the circumferential direction and are made of metal or metal alloy and have a mutual flat contact such that their edges form a single, common and essentially annular blade whose diameter can be continuously adapted to different aortic diameters by a relative movement of the foils in the circumferential direction.

19. The surgical cutting instrument according to claim 17, wherein the at least one foil is supported on an outside of at least one of the one or more supporting arms or guiding arms in the radial direction, and wherein the at least one of the one or more supporting arms or guiding arms is radially adjustable via the actuating mechanism, the at least one foil automatically following a width adjustment in a radially outward direction due to an inherent elasticity of the at least one foil.

20. The surgical cutting instrument according to claim 19, wherein the at least one foil comprises a plurality of foils, and the at least one of the one or more supporting arms or guiding arms comprises a plurality of supporting arms or guiding arms, and wherein a total number of said plurality of foils is equal to a total number of said plurality of supporting arms or guiding arms.

21. The surgical cutting instrument according to claim 19, wherein the at least one foil comprises a first foil on the punch unit and a second foil on the die unit, and wherein the blade of the at least one foil comprises a first blade on the first foil and a second blade on the second foil, the punch unit and the die unit each comprising a foil guide formed by at least one of the one or more supporting arms or guiding arms, wherein the foil guide of the punch unit comprises a first diameter and the foil guide of the die unit comprises a second diameter, wherein the first diameter and the second diameter differ such that the first and second blades move past each other or perform a shear movement.

22. The surgical cutting instrument according to claim 19, wherein the at least one of the one or more supporting arms or guiding arms comprises a fine-meshed, elastic net which follows the width adjustment and forms a closed space during a punching process, in which space the severed aortic valves can be collected and safely recovered.

23. The surgical cutting instrument according to claim 17, wherein the overall length of the at least one foil is, as a whole, longer than a circumference of a maximally adjustable cutting diameter.

24. The surgical cutting instrument according to claim 17, wherein the at least one foil comprises a slanted or tapered foil end.

25. The surgical cutting instrument according to claim 17, wherein the punch unit and the die unit are detachably coupled to each other and distal parts of the punch unit and the die unit can be coupled to or uncoupled from the tool shaft.

26. The surgical cutting instrument according to claim 15, wherein the cutting unit comprises a cutting tool which is rotatably supported around the tool shaft and comprises at least one cutting blade whose radial distance to the rotational axis can be continuously adjusted to different aortic diameters via the actuating mechanism.

27. The surgical cutting instrument according to claim 15, wherein the one or more supporting arms or guiding arms comprises a plurality of axially aligned guiding arms, which are coupled to each other and serve as foil guides or as cutting blade carriers, and can be shifted parallel to the axis of the tool shaft by the actuating mechanism by a parallelogram-type mechanic system.

28. The surgical cutting instrument according to claim 15, wherein the one or more supporting arms or guiding arms can be shifted parallel to the axis of the tool shaft by means of a parallelogram-type mechanic system.

* * * * *